US008476585B2

(12) United States Patent
Galloway

(10) Patent No.: US 8,476,585 B2
(45) Date of Patent: Jul. 2, 2013

(54) MICROTOME UTILIZING A MOVABLE KNIFE IN A RETARDATION FIELD SCANNING ELECTRON MICROSCOPE AND A RETARDATION FIELD SCANNING ELECTRON MICROSCOPE INCLUDING THE SAME

(75) Inventor: Simon Andrew Galloway, Oxford (GB)

(73) Assignee: Gatan, Inc., Warrendale, PA (US)

( * ) Notice: Subject to any disclaimer, the term of this patent is extended or adjusted under 35 U.S.C. 154(b) by 0 days.

(21) Appl. No.: 13/408,054

(22) Filed: Feb. 29, 2012

(65) Prior Publication Data

US 2012/0223228 A1     Sep. 6, 2012

Related U.S. Application Data

(60) Provisional application No. 61/448,338, filed on Mar. 2, 2011.

(51) Int. Cl.
| | | |
|---|---|---|
| *H01J 37/26* | (2006.01) | |
| *H01J 37/28* | (2006.01) | |
| *B01D 59/44* | (2006.01) | |
| *H01J 37/20* | (2006.01) | |
| *H01J 37/18* | (2006.01) | |
| *G01N 1/06* | (2006.01) | |
| *B23K 15/10* | (2006.01) | |

(52) U.S. Cl.
CPC .................. *H01J 37/20* (2013.01); *H01J 37/18* (2013.01); *B23K 15/10* (2013.01); *G01N 1/06* (2013.01)
USPC ........... 250/282; 250/281; 250/287; 250/309; 250/310; 250/307

(58) Field of Classification Search
CPC .... H01J 37/16; H01J 37/18; H01J 37/20; H01J 2237/162; H01J 2237/2006; G01N 2800/52; G01N 33/6851; G01N 1/286
IPC H01J 37/16,18/20, 2237/162, ; G01N 2800/52, G01N 33/6851, 1/286
See application file for complete search history.

(56) References Cited

U.S. PATENT DOCUMENTS

| | | | |
|---|---|---|---|
| 4,377,958 A | 3/1983 | Leighton | |
| 7,714,276 B2* | 5/2010 | Pevsner et al. | ................ 250/282 |

(Continued)

OTHER PUBLICATIONS

FEI Company: "FEI Quanta 600 FEG", Jan. 1, 2006, XP55029690, Retrieved from the Internet: URL:http://www.felmi-zfe.tugraz.at/download/2006_06_Quanta600_FEG_pb.pdf.

(Continued)

*Primary Examiner* — David A Vanore
(74) *Attorney, Agent, or Firm* — Caesar, Rivise, Bernstein, Cohen & Pokotilow, Ltd.

(57) ABSTRACT

A microtome for in situ residence within a chamber of a scanning electron microscope (SEM) and a SEM including the microtome is disclosed. The microtome includes a specimen holder for holding a specimen thereon at high voltage to produce a retardation field thereat and a movable knife. The SEM includes a backscatter electron detector disposed adjacent to specimen holder. The knife arranged is to be carried into engagement with the specimen on the specimen holder to slice a portion of the specimen away to expose a new face of the specimen without interfering with the high voltage on the specimen, and is mounted so that after having engaged the specimen to expose a new face of the specimen it is withdrawn to a retracted position whereupon it does not interfere with the retardation field.

17 Claims, 3 Drawing Sheets

U.S. PATENT DOCUMENTS

| | | | |
|---|---|---|---|
| 2007/0114375 A1* | 5/2007 | Pevsner et al. | 250/282 |
| 2011/0062320 A1* | 3/2011 | Pevsner et al. | 250/282 |
| 2011/0240852 A1* | 10/2011 | Tanner | 250/307 |
| 2012/0145899 A1* | 6/2012 | Matsumoto | 250/310 |
| 2013/0037715 A1* | 2/2013 | Boughorbel et al. | 250/307 |

OTHER PUBLICATIONS

FEI Company: "FEI Quanta 200 FEG", Jan. 1, 2006, XP55029839, Retrieved from the Internet: URL: http://www.personalas.ktu.lt/~tomtamu/files/SEM/2006_06_Quanta_200FEG_pb.pdf.

Winfried Denk et al: "Serial Block-Face Scanning Electron Microscopy to Reconstruct Three-Dimensional Tissue Nanostructure", PLOS Biology, vol. 2, No. 11, Jan. 1, 2004, p. E329, XP55029775, ISSN: 1544-9173, DOI: 10.1371/journal.pbio.0020329 figure 2.

A. Zankel et al: "Ultramicrotomy in the ESEM, a versatile method for materials and life sciences", Journal of Microscopy, vol. 233, No. 1, Jan. 1, 2009, pp. 140-148, XP55029689, ISSN: 0022-2720, DOI: 10.1111/j.1365-2818.2008.03104.x figure 1.

International Search Report for PCT/US2012/027225 mailed Jun. 27, 2012.

* cited by examiner

MICROTOME UTILIZING A MOVABLE KNIFE IN A RETARDATION FIELD SCANNING ELECTRON MICROSCOPE AND A RETARDATION FIELD SCANNING ELECTRON MICROSCOPE INCLUDING THE SAME

CROSS-REFERENCE TO RELATED APPLICATIONS

This utility application claims the benefit under 35 U.S.C. §119(e) of provisional application Ser. No. 61/448,338 filed on Mar. 2, 2011 and entitled "A Microtome Utilizing A Movable Knife For Use In A Retardation Field Scanning Electron Microscope And A Retardation Field Scanning Electron Microscope Including The Same." The entire disclosure of this provisional application is included herein by reference.

FIELD OF THE INVENTION

The invention relates generally to the field of electron microscopy image detection and more particularly to sequential block face imaging in a Scanning Electron Microscope using a retardation field for enhanced imaging.

BACKGROUND OF THE INVENTION

Determining the 3D structure of a specimen is of significant importance in various fields, e.g., biological and materials research. Block face imaging inside the chamber of a scanning electron microscope (SEM) is one way of determining the make-up of such structures. As is known, a higher resolution 2D image can sometimes be obtained in a SEM if the electron landing energy is reduced by applying a negative retardation voltage to the specimen. Accordingly, the application of a retardation field to the specimen is a growing trend in electron microscopy and is being offered routinely by JEOL, PEI and Hitachi on select SEM models. The retardation voltage is applied to the specimen being imaged and this voltage is configurable by the user through a dedicated user interface. The retardation voltage is typically less than the column high tension (energized voltage of electrons leaving the pole piece of the column). The landing energy of electrons on the specimen is close to the difference between these two voltages. When detecting backscattered electrons the associated electric field has a double benefit as the re-energizing of the backscattered electrons stimulates a stronger response by the detector. A common configuration is for the retardation voltage to be applied to the specimen holder which is electrically isolated from the SEM chamber, which remains at ground potential throughout. The retardation field reduces the landing energy of the electrons. However, since the field can never be entirely symmetrical to the pole piece of the microscope, the field typically causes some shift in the position of the beam, in the focus and in the astigmatism of the focused probe.

Utilizing a microtome within the chamber of an SEM making use of a retardation field to take sequential slices of the specimen for block face imaging presents the problem that the knife blade of the microtome, or knife blade holding structure will interfere with the retardation field. This will cause image shift effects between sequential slice images which will degrade the alignment and quality of a 3D "stack" of images.

SUMMARY OF THE INVENTION

In an embodiment, the invention comprises a microtome for in situ residence within a chamber of a scanning electron microscope, the microscope including a specimen holder for holding a specimen thereon at high voltage to produce a retardation field thereat and a backscatter electron detector disposed adjacent to the specimen holder, the microtome including a knife arranged to be carried into engagement with the specimen on the specimen holder to slice a portion of the specimen away to expose a new face of the specimen, the knife being mounted so that after having engaged the specimen to expose a new face of the specimen it is withdrawn to a retracted position whereupon it does not interfere with the retardation field. In a further embodiment, the knife comprises a high impedance material, which, in an embodiment, is diamond.

In a further embodiment, the knife is mounted on a knife holder on a pivoting arm. In a further embodiment the knife is mounted on a knife holder on a linearly moving arm.

In a further embodiment, the specimen holder is arranged to be moved a predetermined distance sequentially with respect to the knife to enable the knife to be brought into engagement with a portion of the specimen to effect sequential slicing and concomitant imaging of the specimen.

In a further embodiment, the invention comprises a scanning electron microscope comprising a chamber, a specimen holder located within the chamber for holding a specimen thereon at high voltage to produce a retardation field thereat, an electron detector disposed adjacent to specimen holder, and a microtome, the microtome including a knife arranged to be carried into engagement with the specimen on the specimen holder to slice a portion of the specimen away to expose a new face of the specimen, the knife being mounted so that after having engaged the specimen to expose a new face of the specimen it is moved to a new position, whereupon it does not interfere with the retardation field. In an embodiment, the electron detector comprises a backscatter detector. In further embodiments, the retardation field is applied to the specimen or the specimen holder. In a further embodiment, the retardation field is applied to a neighboring grid/ring/shroud structure. In a further embodiment, the knife comprises a high impedance material. In a further embodiment, the high impedance material is diamond. In a further embodiment the knife is mounted on a knife holder on a pivoting arm and the knife holder is designed not to interfere with the high voltage applied to the specimen. In a further embodiment the knife is mounted on a knife holder on a linearly moving arm and the knife holder is designed not to interfere with the high voltage applied to the specimen. In a further embodiment, the specimen holder is arranged to be moved a predetermined distance sequentially with respect to the knife to enable the knife to be brought into engagement with a portion of the specimen to effect sequential slicing and concomitant imaging of the specimen.

DESCRIPTION OF THE PREFERRED EMBODIMENT OF THE INVENTION

Figure 1:
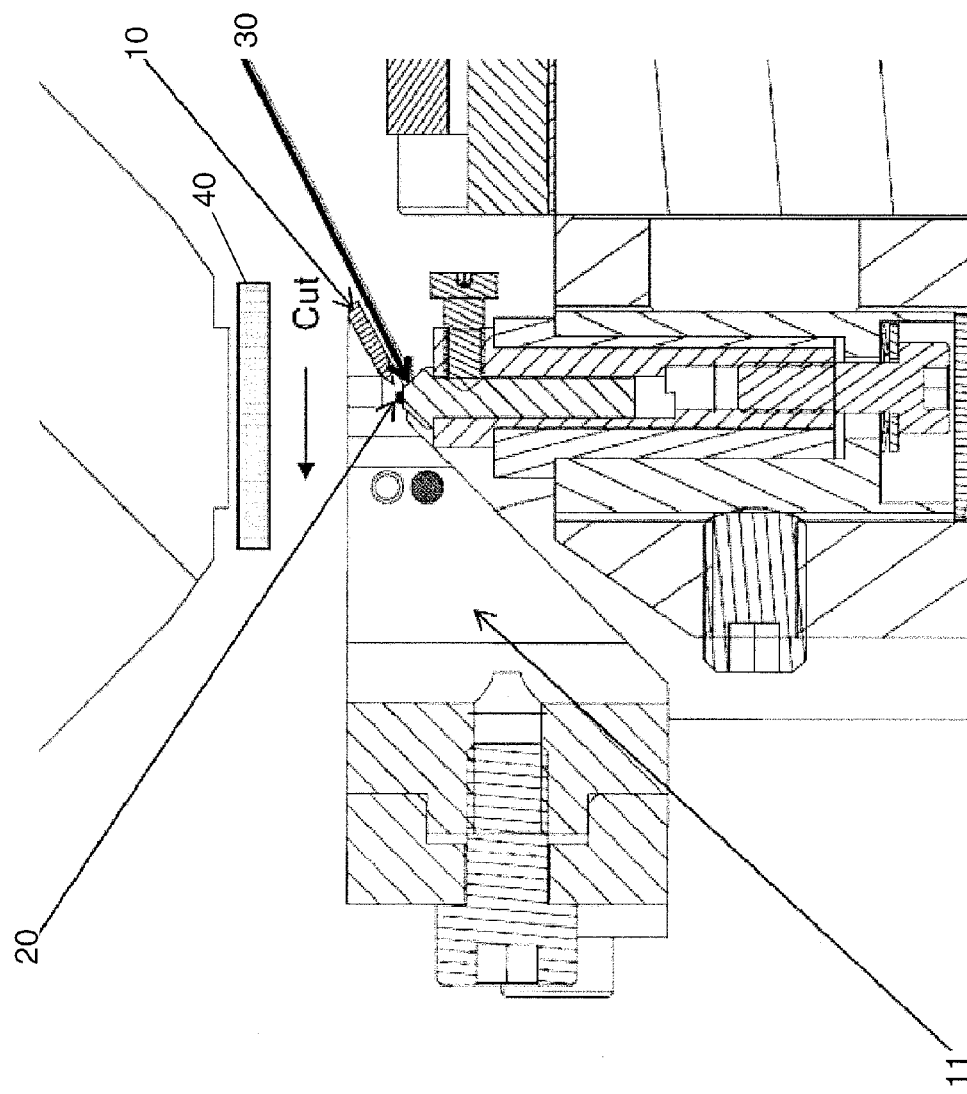
FIG. 1 is an illustration of one portion of a microtome constructed in accordance with this invention shown within the chamber of an SEM making use of a retardation field and showing the knife of the microtome as it is about to take a slice of a specimen for during a sequential block face scanning operation.

The subject invention addresses the problems of interference between the knife blade and the retardation voltage field to enable application of a negative retardation voltage to the specimen when effecting sequential block face imaging (hereinafter referred to as the "SBFSEM technique") to enable higher resolution, well-aligned imaging in 3D, without interfering with the retardation field. Other advantages of utilizing a retardation voltage for SBFSEM 3D imaging include lower landing energy, which facilitates sampling the imaging signal from a shallower depth, i.e. the third dimension. The retardation voltage also enables the column to operate in a mode less sensitive to environmental fields which can hamper resolution, and it facilitates higher quality image collection for a given electron beam scanning speed, due to the associated improvements in the back scattered electron detector.

To that end, an embodiment of the subject invention consists of a modified microtome in-situ inside the SEM chamber. A sharp knife forming a portion of the microtome shaves a prescribed layer from the top of the specimen and the freshly revealed block face is imaged by scanning an electron or similar particle beam and measuring the interaction of the beam with the specimen. In particular, the subject invention operates by bringing a sharp knife between the specimen and the pole piece of the SEM. With this design the specimen is mounted on an electrically isolated specimen holder with an applied retardation voltage. The specimen does not move a macroscopic distance, or require repositioning (in the XY plane) between sequential cuts of the knife. Instead the mechanism holding the knife moves away a macroscopic distance from the specimen in order not to interfere with the retardation field during imaging. Moreover, the mechanism holding the knife structure does not interfere with the high tension applied to the specimen and only the knife itself contacts the specimen to remove the desired top surface layer. For example, if there is a temporary conductive pathway between the specimen at high tension and some other conductive body at lower potential or earth, then the field will be altered, and this will cause the resolution and intended position of the electron beam to change in an uncontrolled fashion which will impact the automated acquisition of sequential images through the block face of similar quality and spatial position. To avoid this effect, the knife is fabricated or made from a highly insulating material and does not have any conductive coating. Furthermore the tool for holding the knife is designed to prevent a high tension discharge event by means of the shape, surface finish, conductivity and proximity of said surfaces to neighboring surfaces during the pivot movement when the knife is retracted from the specimen area.

The subject invention provides the following advantages over prior art devices for effecting the SBFSEM technique. In particular, it enables higher resolution results in 2D when imaging the specimen in the plane of the cut block face as well as providing higher resolution in 3D. Moreover, the subject invention facilitates faster results for a given 2D or 3D resolution. In addition to those advantages, the subject invention reduces the energy dose into the specimen.

When using the SBFSEM technique for resin-embedded specimens, the energy dose must remain low in order for the new block face to remain smooth and for the image to have no resin overdose artifacts. Lowering the dose by reducing the electron flux rather than the landing energy removes necessary detail from the signal so can be counterproductive. The subject invention enables reduction of the energy dose into the specimen without loss of image detail. In addition, since the subject invention allows the specimen to be sequentially cut using the in-situ microtome in an automated fashion, that action can be accomplished without need for iterative correcting of focus, astigmatism or macroscopic re-alignment. The subject invention also allows the SBFSEM technique to be achieved when lowering the landing energy of the electrons/ions without degradation to the absolute focusing power of the microscope. Further still, the subject invention allows the SBFSEM technique to be accomplished using a backscattered electron detector which samples electrons/ions close to their original energy when leaving the pole piece rather than at the reduced landing energy. Further yet, the subject invention allows other signals to be sampled by providing a clear view of the specimen. Lastly, the subject invention enables clearing the knife a macroscopic distance from the specimen, which allows the specimen to be raised a macroscopic distance to allow higher resolution imaging, or higher yield performance from detectors optimized for short working distance.

The SEM can be any conventional device, such as those commercially available from a range of vendors. The SEM includes a chamber in which the SEM's imaging detector, e.g., a backscatter electron detector, is located along with the holder for the specimen to be imaged. The specimen holder is in the form of a platform or some other base and is conductive so that a high tension retardation voltage can be continuously applied to the specimen via the holder. The specimen holder is insulated from the rest of the SEM structure (e.g., chamber and pole piece), so that only it is at high voltage (tension). In accordance with one aspect of this invention the specimen holder forms a portion of the microtome of this invention. Alternatively, it may form a portion of the SEM itself. In either case the specimen holder is arranged to be moved a microscopic distance, e.g., 50 nm, with respect to a knife of the microtome, so that the microtome's knife can be brought into engagement with the specimen to slice a portion of the specimen away and thereby expose a new face of the specimen to be imaged.

Figure 2:
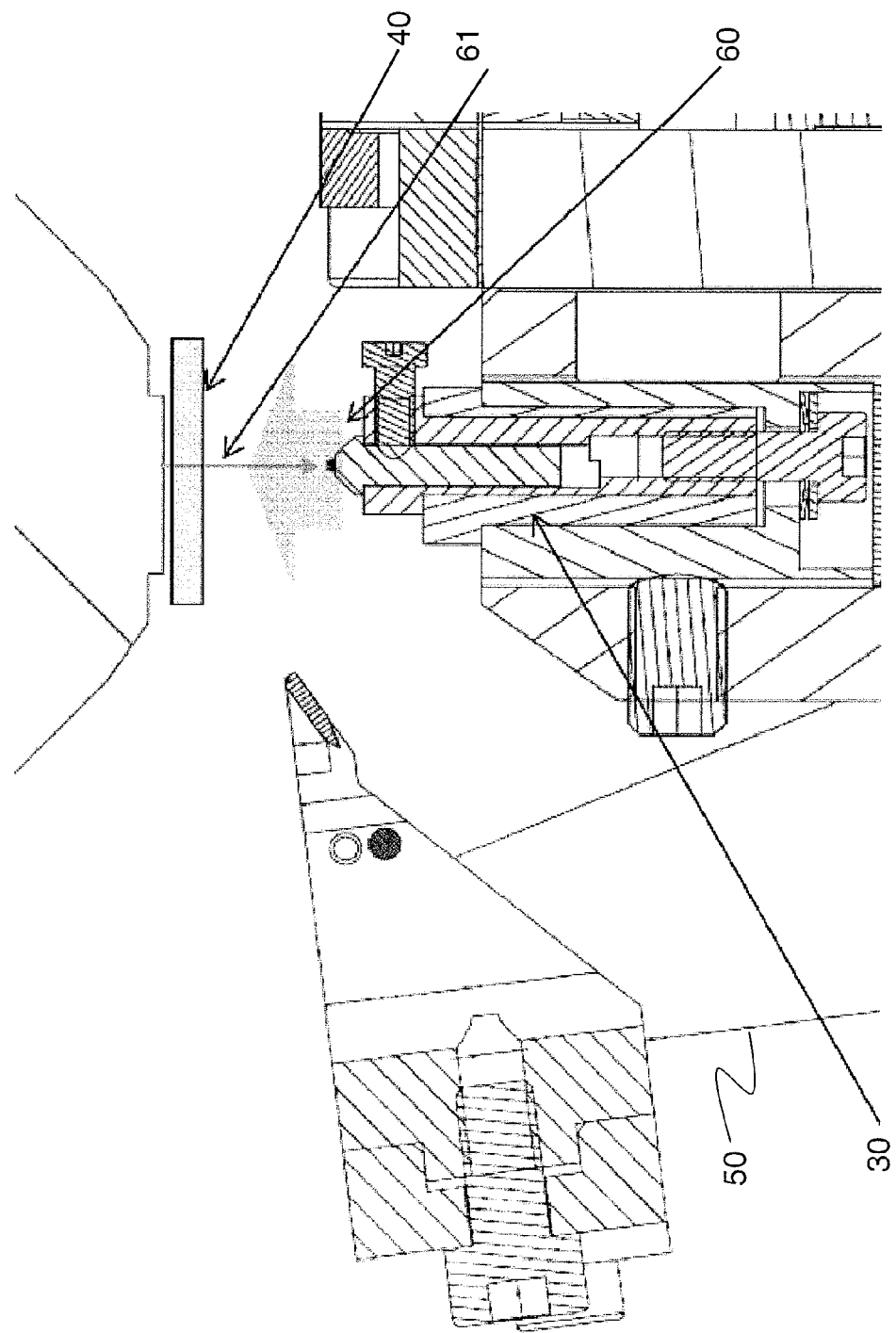
FIG. 2 is an illustration, similar to FIG. 1, but showing the microtome after a portion of the specimen has been sliced off (and removed) thereby exposing a new block face of the specimen for scanning.

In FIGS. 1 and 2 there is shown the microtome of this invention with its knife 10 (e.g., blade) located immediately adjacent a specimen 20 mounted on the specimen holder 30 so that it can be carried into engagement with the specimen 20 (as will be described shortly) to slice the specimen and expose a new block face of the specimen to the incident beam 61. As will be appreciated by those skilled in the art, in this position the knife 10 and associated holder 11 is located below the backscatter electron detector 40 and in a position that would interfere with the retardation field produced by the voltage on the specimen holder. To avoid that adverse effect, the knife 10 is mounted on a movable arm 50 (e.g., a pivoting structure) which carries the knife into engagement with the specimen. In particular, the movable arm 50 is arranged so that after the knife 10 has sliced off a defined thickness portion of the specimen 20 to expose a new block face, the knife is then located in a cleared position, a macroscopic distance from the specimen holder, such as shown in FIG. 2. In this position the knife does not interfere with the retardation field 60, so that accurate imaging of the exposed specimen face can be accomplished. Moreover, the knife is preferably formed of a material that is not conductive or is of a high impedance, e.g., diamond, and does not include any conductive coating so that the act of cutting by the knife does not discharge the specimen to earth potential. Further still, as mentioned above, the knife holder is designed and constructed so as not to provide a discharging mechanism, for example by means of an arc at any point in the microscopic or macroscopic pivot movement.

Consecutive slices of the specimen can be accomplished automatically by the microtome effecting the repeated indexing or movement of the specimen holder with respect to the knife. Thus, after the exposed block face just cut by the knife has been imaged, the knife blade is brought back to the position shown in FIG. 1 and the platform or specimen holder moved or indexed upward a predetermined distance, equal to the thickness of the slice of specimen to be removed. After that has been accomplished, the knife is again brought into engagement with the specimen to expose a new block face, and the knife is retracted to the position shown in FIG. 2 so that the new block face can be imaged.

Figure 3:
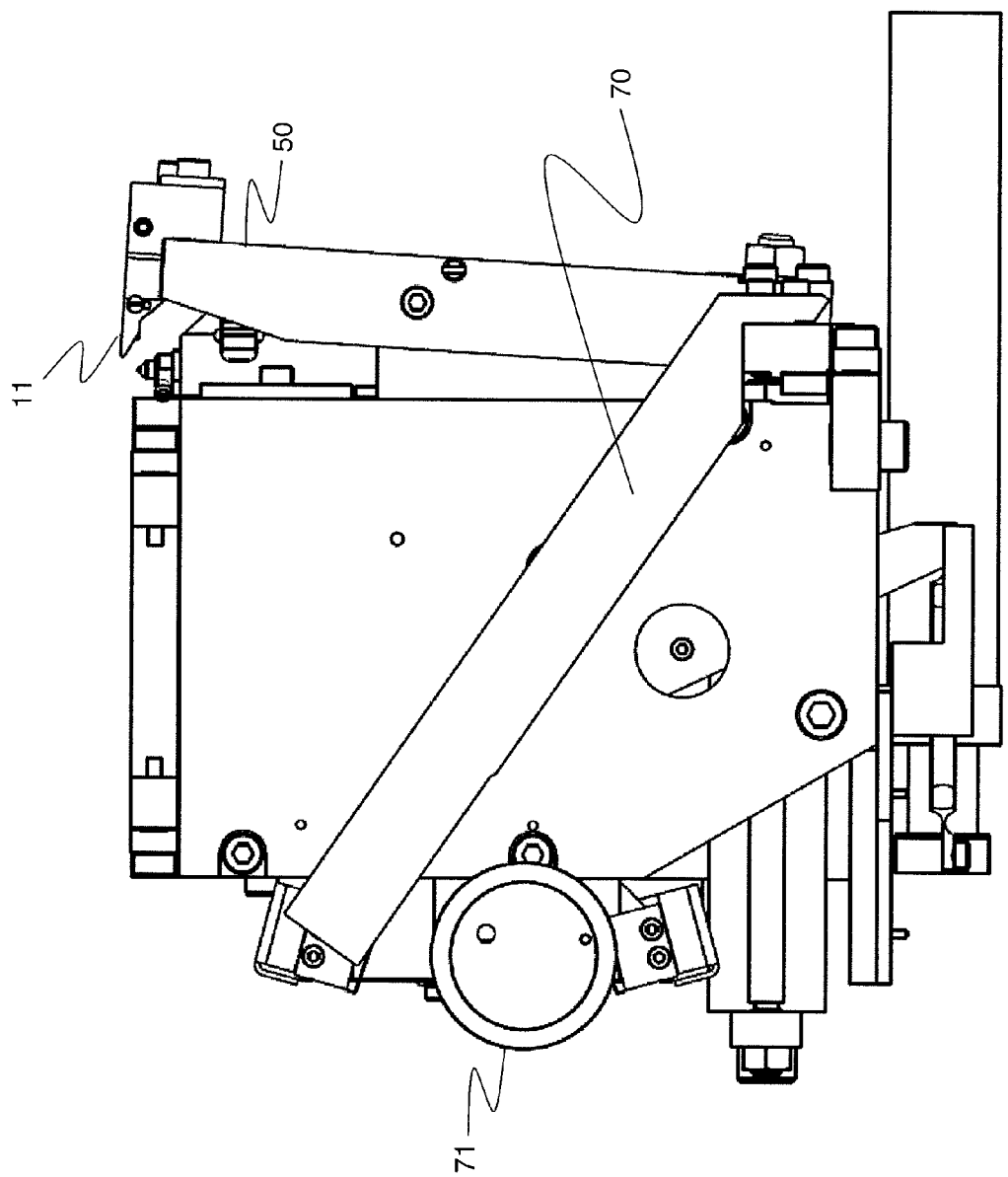
FIG. 3 is an illustration of a larger portion of the microtome of FIGS. 1 and 2, showing an actuation mechanism for moving the knife.

With respect to FIG. 3, there is shown a further view of an exemplary sample holder/microtome assembly. In this view, the knife support arm 50 is shown retracted from the sample 20. Offset cam 71 is rotated by a DC motor and causes the side arm 70 to clear the knife arm away from the microtome body.

It should be noted at this juncture that such components described herein are merely exemplary of various components that can be utilized to accomplish the ends of this invention.

For example, while the exemplary preferred embodiment applies the retardation voltage to the specimen/specimen holder, other arrangements can be used. For example, it is contemplated that the invention may entail applying a retardation field to a neighbouring grid/ring/shroud, etc., independent of the specimen. Moreover, while the mechanism for moving the knife is shown as a pivoting member, it is contemplated that the knife can be moved in a linear path by any suitable means, e.g., a linearly moving arm or other mechanism.

As should be appreciated by those skilled in the art, the SBFSEM technique using this invention can work with an insulating, partially conducting or fully conducting specimen. If the specimen is not fully conducting then a more reproducible retardation field is expected after every cut if the specimen is central to the imaging axis to the microscope, is symmetrical, and if the sides of the specimen are conductively coated. As a further aid to maintaining a consistent retarding field between each cutting operation, it is contemplated that a symmetric metal shroud would be provided to cover the immediate sides of the specimen. The shroud and specimen may be at the same or different voltage potentials so as to benefit the uniformity of the field. Moreover, the rim of the shroud (e.g., a truncated or sliced conical shape) would be at a height to allow the knife to operate without impediment.

The invention claimed is:

1. A microtome for in situ residence within a chamber of a scanning electron microscope, the microscope including a specimen holder for holding a specimen thereon at high voltage to produce a retardation field thereat and a backscatter electron detector disposed adjacent to the specimen holder, the microtome including a knife arranged to be carried into engagement with the specimen on the specimen holder to slice a portion of the specimen away to expose a new face of the specimen, the knife being mounted so that after having engaged the specimen to expose a new face of the specimen it is withdrawn to a retracted position whereupon it does not interfere with the retardation field.

2. The microtome of claim 1 wherein the knife comprises a high impedance material.

3. The microtome of claim 2 wherein the high impedance material is diamond.

4. The microtome of claim 1 wherein the knife is mounted on a knife holder on a pivoting arm.

5. The microtome of claim 1 wherein the knife is mounted on a knife holder on a linearly moving arm.

6. The microtome of claim 1 wherein the specimen holder is arranged to be moved a predetermined distance sequentially with respect to the knife to enable the knife to be brought into engagement with a portion of the specimen to effect sequential slicing and concomitant imaging of the specimen.

7. The microtome of claim 1, wherein the specimen holder is insulated from the remaining portion of the microtome, which is held at ground potential.

8. A scanning electron microscope comprising a chamber, a specimen holder located within the chamber for holding a specimen thereon at high voltage to produce a retardation field thereat, an electron detector disposed adjacent to specimen holder, and a microtome, the microtome including a knife arranged to be carried into engagement with the specimen on the specimen holder to slice a portion of the specimen away to expose a new face of the specimen, the knife being mounted so that after having engaged the specimen to expose a new face of the specimen it is moved to a new position, whereupon it does not interfere with the retardation field.

9. The scanning electron microscope of claim 8 wherein the electron detector comprises a backscatter detector.

10. The scanning electron microscope of claim 8 wherein the retardation field is applied to the specimen or specimen holder.

11. The scanning electron microscope of claim 8 wherein the retardation field is applied to a neighboring grid/ring/shroud structure.

12. The scanning electron microscope of claim 8 wherein the knife comprises a high impedance material.

13. The scanning electron microscope of claim 12 wherein the high impedance material is diamond.

14. The scanning electron microscope of claim 8 wherein the knife is mounted on a knife holder on a pivoting arm and the knife holder is designed not to interfere with the high voltage applied to the specimen.

15. The scanning electron microscope of claim 8 wherein the knife is mounted on a knife holder on a linearly moving arm and the knife holder is designed not to interfere with the high voltage applied to the specimen.

16. The scanning electron microscope of claim 8 wherein the specimen holder is arranged to be moved a predetermined distance sequentially with respect to the knife to enable the knife to be brought into engagement with a portion of the specimen to effect sequential slicing and concomitant imaging of the specimen.

17. The scanning electron microscope of claim 8 wherein the specimen holder is insulated from the remaining portion of the microtome, which is held at ground potential.

* * * * *